United States Patent [19]

Stickl

[11] 4,049,793
[45] Sept. 20, 1977

[54] PREPARATIONS FOR LOCAL TREATMENT OF ACNE VULGARIS

[76] Inventor: Helmut Stickl, Starenweg 6, 8033 Krailling, near Munich, Germany

[21] Appl. No.: 665,717

[22] Filed: Mar. 10, 1976

[30] Foreign Application Priority Data

Mar. 14, 1975 Germany .............................. 2511258

[51] Int. Cl.$^2$ ..................... A61K 35/00; A61K 39/40; A61K 39/00; A61K 39/02
[52] U.S. Cl. ........................................ 424/115; 195/96; 424/87; 424/88; 424/92; 424/93; 424/123

[58] Field of Search ..................... 424/88, 93, 92, 115, 424/87

[56] References Cited

PUBLICATIONS

Chemical Abstracts, vol. 80, (1974), 6903v.

Primary Examiner—Frederick E. Waddell
Attorney, Agent, or Firm—DeLio and Montgomery

[57] ABSTRACT

The invention provides a novel preparation, preferably in ointment form, for local treatment of acne vulgaris, methods for production of the same and method for treatment of acne vulgaris therewith.

11 Claims, No Drawings

PREPARATIONS FOR LOCAL TREATMENT OF ACNE VULGARIS

The invention concerns preparations, particularly in the form of an ointment or a face lotion, which contain an active substance with which acne vulgaris can be treated locally. These preparations are suitable for lighter forms of acne, particularly for follicular acne and papular acne, acne in the incipient stage, as well as a supplemental treatment in oral acne antigen therapy.

Acne vulgaris is an adolescent disease which can last into the forties. Hormonal, dietetic and constitutional factors play a part in the genesis of acne, in addition to acne bacteria. Therapy started heretofore with these individual pathogenic factors: thus diet instructions were worked out, but they were only successful when accompanied by other treatment methods. Girls were given ovulation inhibitors, but these were likewise only partly successful. Recently a long-term treatment with antibiotics, preferably tetracyclines, led to further progress in the treatment of acne. But in about 60% of the cases the patients became accustomed to the antibiotics and fungus colonies soon appeared in the mouth and at the genitals (in women up to 20%).

Another possibility of acne treatment consists of vitamin A-alcohol in local application and vitamin A in systematic application. Vitamin A has a desquamating effect with regeneration of the skin. But this treatment can only be tolerated by about half of all patients and is therefore again successful only in half of the patients. This means that healing or improvement by vitamin A — treatment is achieved in only 25% of all acne patients.

Preparations for the oral antigen treatment of acne are known from German Pat. Nos. 2,213,677 and 2,306,223. Here the oral application of the acne-bacteria antigens resulted in densensitization and immunization against the Coryne bacterium acnes.

In many cases, particularly in incipient acne, local treatment is sufficient, however.

There are therefore a number of ointments and essences for the treatment of acne. The essential ingredients of these therapeutic agents are disinfectants, desquamatives and abrasives, as well as cortisone in ointment form. The latter is suitable to reduce the allergic and inflammatory symptoms of acne and to bring them partly under control, but it has the disadvantage that it enhances the growth of acne bacteria and other secondary germs (for example, skin staphylococci). The disinfectants reduce locally the germ flora. Cortisone also leads to atrophy of the skin on prolonged use, so that the application of cortisone is limited as far as intensity and duration of the treatment are concerned. Desquamation ointments, as well as ultraviolet radiation of the skin can only have a temporary effect, since the acne appears again as a rule even before the treatment is completed.

The object of the invention is to provide a preparation for the local treatment of acne which is gentle to the skin and has at the same time a germ-reducing and desensitizing effect.

It was found that culture media of acne bacteria, particularly if acne bacteria of different strains have been grown for a long time in the same culture medium up to the end of germ multiplication, contain a substance which is hereinafter called "acnecine" and which has an inhibiting effect on acne bacteria. When added to fresh media, it inhibits, in concentrations of up to 1:2000, the newly inoculated acne bacteria in their growth. Acnecine cannot be dialyzed, it inhibits only the Coryne bacterium acnes, is heat-resistant, and cannot be precipitated with ammonium sulfate.

The non-dialyzable, antigenic substances remaining in the dialysis tube are lipopolysaccharides and proteides of the acne bacteria. An exact chemical definition of the non-homogeneous organic substance is not yet possible.

The active factor acnecine can be obtained very easily be centrifuging the acne bacteria foam liquid cultures.

The nutrient medium of the liquid cultures is dialyzed, for example, with cellophane-dialysis tubes for serum dialysis, so that low-molecular cleavage products, like amino acids, glucose of the nutrient medium, peptone, glycerin, etc. under a molecular weight of about 10,000 to 12,000 and particularly common salt are eliminated. By concentrating the liquid volume, preferably by dialysis or freeze-drying, the active factor acnecine can be concentrated. It can furthermore be filled with ammonium sulfate until it is completely saturated. It does not flocculate by boiling, but it loses about two-thirds of its effectiveness. This active factor can now be used in liquid form as a face lotion or it can be incorporated in an ointment for acne treatment. It was found expedient to prepare the ointment in the form of an oil-in-water emulsion with acnecine, since a longer duration of action can be expected here.

As an ointment base, any hydrophilic ointment can be used in which at least 20% of an aqueous solution can be incorporated. Preferably 20 to 40% of the aqueous acne solution are incorporated into the ointment base. Preservatives can be used, such as ethyl alcohol, glycerin or merfen, a Hg-containing preservative. Resorcinol was found to be suitable as a disinfectant.

Dehydrated wool fat, lanolin, particularly in a preparation with emulsifying cetylstearylalcohol, e.g. Lennette N(R), are just as suitable. The addition of viscid paraffin and white vaseline is in this case not necessary, but they can be added in any amount to further improve the ointment.

For example, 60 parts hydrophilic lanolin ointment (e.g. Lanette N) are mixed in a mixer with 5 parts glycerin, 5 parts 96% isopropyl alcohol, and 30 parts of the aqueous acnecine solution to form an easily spreading creme. Isopropyl alcohol and glycerin serve as preservatives. Instead of isopropyl alcohol, undenatured ethyl, alcohol can also be used, for example.

In light cases of acne a mild abrasive treatment with a fine-grained, abrasive paste containing resorcinol (e.g. Brasivil-fine) can be used. Then the acnecine creme or ointment is applied as a skin-protecting after-treatment. The relaxing inflammation-reducing effect was considered by all patients treated so far, although more than 60, as pleasant.

A dilution series of acnecine was produced in decreasing concentrations (1:10, 1:20, 1:40, etc.) in thioglycolate bouillon. Completely filled test tubes were inoculated with 0.1 ml of a suspension of acne bacteria containing about 200,000 germs. The test tubes were sealed with a tightly sealing rubber stopper under the sharp jet of a inclined bunsen burner (the small air chamber between the nutrient medium and rubber stopper was thus deprived of oxygen). These test tubes were then placed into the incubator at 35° C. The cultures were inoculated with the Coryne bacterium acnes, Beck strain, Gerrath strain and Vogen strain (group B), as well as Coryne bacteria of the groups A and B freshly supplied by the patients. The growth was evaluated after two days; turbidity as seen in the acnecine-free controls. Further evaluation on the fourth day after inoculation showed that cultures with a higher acnecine content were clear, while those with a diminishing acnecine action were cloudy, due to the growth of bacteria. The acnecine concentration was determined with the first visible turbidity, and the acnecine dilution with a density of germ growth which corresponds to that of the control. An inhibiting concentration was assumed at the acnecine dilution at which no germ-related turbidity of the nutrient medium was visible on the 4th day after inoculation.

The acnecine solution inhibits all acne strains, and was tested on over 18 freshly isolated acne bacteria strains. The effectiveness of the preparation according to the invention consists not only in the local inhibition of germ growth, but also in a cool desensitization of the skin due to the presence of soluble antigens of the acne bacteria (antigenic metabolites, components of the acne bacteria in aging cultures). This accounts for the disappearance of the red areolas around the acne efflorescences (allergic inflammable reactions) of the skin, as well as the disappearance of itching and tension of the skin, indicated by the patients.

A germ-inhibiting effect is thus achieved without the undesirable side effects of the disinfectants or antibiotics, as well as a skin-relaxing effect, which influences the allergic inflammation. With normalized physiological skin conditions, the acne can heal better. The undesired effect of the cortisone derivatives, which hinder the healing processes, is eliminated here. Likewise, skin atrophy caused by corticosteroids is not expected.

A preferred production method for the preparations according to the invention consists of inoculating nutrient bouillon with Coryne bacteria acnes of at least two different strains, adding glycerin at a pH of 5.5 to 6.0, effecting the growth under anaerobic conditions, incubating at about 35° C for about 9 to 16 days, and effecting sedimentation of the germs in the cold for about 8 to 12 hours, separating the clear supernatant, and purifying by centrifugation, killing the remaining germs by heating to 60° C for about one hour, introducing into dialysis tubes and concentrating the volume, and then mixing the concentrated culture volume with customary ointment bases after testing for sterility and absence of harmful substances.

We will now describe the production and testing of the preparations according to the invention by way of several examples.

EXAMPLE 1

One liter of a 2% standard nutrient bouillon with 5% glycerin and a pH of 5.5 to 6.0 was inoculated with acne bacteria of two different strains, a freshly isolated wild strain of the third laboratory passage of patients and the strain V(L), an attenuated laboratory strain.

It is also possible to inoculate the liquid medium with about equal inoculation amounts (3–6 × $10^9$ germs) of several acne bacteria strains.

The growth took place under anaerobic conditions. Incubation was conducted in the incubator at 35° C for 9–16 days. It was found that a better production of acnecine is possible, if the incubation is effected at somewhat lower temperatures (34°–35° C) than usual (37.5° C), After 4 days, the acne culture had reached the peak of its growth, after 9 days no additional growth was found anymore.

Presedimentation of the germs was effected permitting the culture to stand in the cold (8–12 h), where the acne bacteria occupy as a silvery shining bulk in the lower quarter of the vessel. The clear yellowish supernatant can be easily pippeted off and then purified by centrifuging (4000 g/20'), killing any remaining germs by heating to 60° C. for 1 hour. This was then introduced, under sterile conditions, into cellophane dialysis tubes of 8–12 cm width with a permeability for molecules of 10,000 to 15,000. The contents of the dialysis tube was stirred briefly to eliminate the salts (twice in bi-distilled water with 40 fold dilution effected for 20 minutes each). Then the dialysis tubes were suspended in a large freshly defrosted refrigerator. After 48 hours about 60 to 80% of the liquid had evaporated in the dialysis tubes and had been deposited on the refrigerating unit as a coat of ice. The volume decreases to one-third to one-fifth of its original size, hence to 200–300 ml.

Final dialysis under stirring against the 10-fold amount of phosphate-buffered (m/95 primary-secondary phosphate buffer according to Sorensen) physiological salt solution was conducted for 20 minutes for cosmetic equalization. This culture volume, which was concentrated by evaporation dialysis, was the acne batch, for example, for the production of the acne ointment. Testing was then conducted for sterility and absence of harmful substances (injection of 5 cc into the abdominal cavity of guinea pigs of ab. 200 g).

The above described production of the active factor according to the invention can be simplified by effecting the concentration of the volume by evaporation dialysis in the refrigerator. Brief dialysis can be effected in a 10 fold amount of distilled water or physiological salt solution. The dialysate still contains some glycerin, which does not interfere, however, with the production of the ointment.

Best results are obtained with the simplified production method of the acnecine ointment by concentration of the dialysate, 20 minutes dialysis against physiological salt solution, and addition of 5% glycerin to the ointment as a preservative and softener. This preparation is effective, stable and can be easily rubbed on the skin of the face.

Another possibility for the production of a creme consists in adding tragacanth, a vegetable mucilage. 5% of tragacanth can be added to the aqueous acnecine batch, as well as 5% glycerin as a preservative. Hot hydrophilic ointment is stirred in so that the latter is then only 50%. A whitish-yellowish creme is obtained.

The production of a face lotion starts with the same acnecine batch. 5% glycerin and 30% alcohol are added. The face lotion is applied after cleaning the skin in the morning, preferably with a disinfecting mild abrasive paste (e.g. Brasivil fine) and letting it dry. If necessary, a skin creme can be applied in addition. The addition of glycerin improves the adhesion of acnecine.

The suggested dose for cheeks, forehead and for the jaw-chin region is an ointment extrusion of 1 cm each. One application of the acnecine ointment in the morning is sufficient.

Consumption of the acnecine ointment in the above described production is low. For the face about 0.4 to 0.6g are used per application. It is important that the acnecine ointment is applied on the skin while it is still moist, (for example, after treatment with the abrasive paste, e.g. Brasivil fine). Since the original acne batch is present in the ointment in a dilution of about 1:5, but has a bacteria-inhibiting effect of at least 1:640, effective amounts of acnecine are used in any case on the facial skin.

Test results a. Antigenic activity

In guinea pigs sensitized against acne bacteria (two inoculating injections, i.m.; i.p. of $5 \times 10^6$ to $10^7$ each with acne bacteria of a mixed culture of several acne bacteria strains) the concentrated dialysate, after intracutaneous injection of 0.1 ml, leads to skin reactions with reddening and swelling of more than 20 mm in diameter. Compared to the negative controls (physiological salt solution) the positive skin test can be considered as proof of the antigenicity of the concentrated dialysate.

b. Germ inhibition

The inhibiting effect on acne bacteria is the decisive criterion for the usability of an acne treatment preparation. The dialysate was added in dilutions of 1:20 to 1:2560 to the agar of Fortner plates or to liquid cultures, followed by inoculation with a rapidly growing well-adapted acne bacteria strain (Beck or Garrath). Comparison was made with controls without addition of dialysate. Preparations which did not show an inhibiting effect of at least 1:640 within an incubation period of 4 days at 37° C were discarded. Dialysates with an acnecine-action (inhibition of the growth of Coryne bacterium acnes, Beck strain) of over 1:2000 were preferred for the further processing.

Even with high acnecine concentrations, there was no bactericidal action, only a retardation of the growth and a time limited inhibition of acne bacteria. Skin staphylococci (*staphylococcus albus*) growing under aerobic conditions were not effected.

EXAMPLE 2

An oil-in-water emulsion in ointment form was produced which contained 20% of the acnecine starting solution a. Hydrophilic ointment: emulsifying cetylstearyl alcohol 30.0% by weight

| viscid paraffin | 35.0% |
|---|---|
| white vaseline | 35.0% | b. Mixing of a) with the acnecine batch at 50° C in the mixer in a ratio of 60:40. Before mixing with the hydrophilic ointment, a preservative or any other additive or auxiliary substance can be added to the acnecine batch.

The application of the preparations according to the invention are described below by way of example.

EXAMPLE 3

On a 13 year old girl with follicular acne in the incipient state, with individual, already inflamed papules with hornified follicles and comedones, an acnecine ointment, prepared with Brasivil fine according to example 1, was applied after the morning cleaning of the skin. The efflorescenses and the inflamed follicles disappeared 3 to 4 days after the beginning of the treatment.

EXAMPLE 4

After two tablet treatments, the appearance of the acne changed in a 19 year old student, who had been treated unsuccessfully for 4 years. The large pumples, papules and nodes were replaced by numerous small, inflammed follicles and nodules. At the same time, dry comedones were formed (so-called blackheads). Further treatment with acne tablets could not fully eliminate this residual condition. Daily application of the acnecine ointment, once in the morning after the cleaning of the skin with a fine-grained disinfecting abrasive paste (e.g. Brasivil fine) yielded a smooth skin after 14 days.

EXAMPLE 5

The subject was a 37 year old woman, who had acne since she was 12, particularly on the face and shoulders. Numerous scars were visible. After exhausting all therapeutic possibilities, she was now resigned to a therapeutic nihilism. Since her 32nd year, after the birth of a child, the acne appeared only weakly and briefly before her menstruation period. She had inflamed follicles with slight painful tension and sometimes itching, particularly on the forehead.

Upon the first symptons of a recurrence, acnecine ointment was applied twice daily; the result was no tension pains anymore. The skin remained substantially clear. Complete healing of the acne could not be achieved, however. Minor recidivatives occurred, particularly at the beginning of the winter, but they were lighter than the previous ones and required no further treatment.

EXAMPLE 6

The subject was a 16 year old student with acne papulo-pustolosa. About 5 days after the start of the tablet treatment (antigen tablets) the subject experienced great exacerbation of the acne with feelings of tension of the skin and itching. Application of the acnecine ointment twice daily showed subjective improvement already on the first day, and after 2 days the efflorescenes had clearly diminished. Further treatment of the acne comprised one-time application of the acnecine ointment in the morning following cleaning of the skin with a mild and disinfecting abrasive paste (Brasivil fine).

In the course of the treatment with acne antigen tablets, there is generally a temporary appearance of the acne efflorescenes (so called "acne-reaction"). The acnecine ointment feels particularly pleasant and relaxing and is useful as a supplementary treatment.

The effectiveness of the acnecine ointment can be improved in many cases if the skin pores are opened first with a mild abrasive paste (e.g. Brasivil fine).

What is claimed is:

1. A preparation for the local treatment of acne vulgaris comprising, in combination with a suitable vehicle, about 20-40% by weight of an active substance obtained by:
    a. growing Coryne bacteria acnes in a liquid growth medium under anaerobic conditions at pH 5.5 to 6.0 with incubation at 35° C for up to 9–16 days until the multiplication peak has passed,
    b. separating acne inhibitor acnecine discharged by the growth of said bacteria into said growth medium as an acnecine-containing liquid from said bacteria and other accompanying substances in said growth medium, and
    c. concentrating said acnecine-containing liquid into an acnecine concentrate comprising said active substance.

2. A preparation of claim 1, wherein said acnecine-containing liquid is purified and concentrated by centrifuging the solid components and by dialysis.

3. A preparation of claim 1, wherein said acne inhibitor acnecine is obtained as an acnecine-containing liquid by centrifuging said bacteria by dialysis or sedimentation of said bacteria and decanting the supernatant acnecine-containing liquid.

4. A preparation of claim 1, wherein said acnecine-containing liquid is concentrated into said acnecine concentrate by lyophilization or evaporation dialysis.

5. A method for the production of preparations for the local treatment of acne vulgaris, particularly in the form of ointments and face lotions comprising the steps of:
 a. growing Coryne bacteria acnes in a liquid growth medium under anaerobic conditions at pH 5.5 to 6.0 with incubation at 35° C for up to 9–16 days until the multiplication peak has passed,
 b. separating the acne inhibitor acnecine discharged by the growth of said bacteria into said growth medium, as anacnecine-containing liquid, from said bacteria and other accompanying substances in said growth medium,
 c. concentrating said acnecine-containing liquid into an acnecine concentrate, and
 d. incorporating about 20–40% by weight of said acnecine concentrate in a water-in-oil emulsion by adding suitable emulsifiers.

6. The method of claim 5, wherein said acnecine-containing liquid is purified and concentrated by centrifuging the solid ingredients and by dialysis.

7. The method of claim 6, wherein 20–40% of said acnecine concentrate is incorporated in about 70–50% of an oil base and about 10% of other cosmetic components.

8. The method of claim 5, wherein said acne inhibitor acnecine is obtained as an acnecine-containing liquid by centrifuging said bacteria and decanting the supernatant.

9. The method of claim 5, wherein said acnecine-containing liquid is concentrated into said acnecine concentrate by lyophilization or evaporation dialysis.

10. A method for treatment of acne vulgaris comprising local application on the skin of a therapeutically effective amount of a preparation of claim 1.

11. The preparation of claim 1, wherein said acnecine concentrate is incorporated in a water-in-oil emulsion by adding suitable emulsifiers.

* * * * *

UNITED STATES PATENT AND TRADEMARK OFFICE
CERTIFICATE OF CORRECTION

PATENT NO. : 4,049,793
DATED : September 20, 1977
INVENTOR(S) : Helmut Stickl

It is certified that error appears in the above-identified patent and that said Letters Patent are hereby corrected as shown below:

| | |
|---|---|
| Column 2, line 10 | place quotation marks (") around the word --"acnecine"-- |
| Column 2, line 11 | delete the word "foam" and substitute in its place the word --from-- |
| Column 2, line 20 | place quotation marks (") around the word --"acnecine"-- (which is hyphenated at the end of the line) |
| Column 2, line 57 | place quotation marks (") around the word --"acnecine"-- |
| Column 3, lines 65-66 | "ofacne-cine" should read --of "acne-cine"-- |
| Column 3, line 67 | the comma (,) at the end of the line should be a period --.-- |
| Claim 1, col. 6, line 61 | insert the word --the-- between "separating" and "acne" to read --separating the acne-- |

Signed and Sealed this

Sixth Day of December 1977

[SEAL]

Attest:

RUTH C. MASON
Attesting Officer

LUTRELLE F. PARKER
Acting Commissioner of Patents and Trademarks